United States Patent [19]
Mobley et al.

[11] Patent Number: 6,066,480
[45] Date of Patent: May 23, 2000

[54] METHOD FOR HIGH SPECIFIC BIOPRODUCTIVITY OF α,ω-ALKANEDICARBOXYLIC ACIDS

[75] Inventors: David Paul Mobley, Schenectady, N.Y.; Gary Keith Shank, Rocky Hill, Conn.

[73] Assignee: General Electric Company, Schenectady, N.Y.

[21] Appl. No.: 09/157,669

[22] Filed: Sep. 21, 1998

[51] Int. Cl.$^7$ .................................................... C12P 7/44
[52] U.S. Cl. .................................................... 435/142
[58] Field of Search ............................................. 435/142

[56] References Cited

U.S. PATENT DOCUMENTS

| | | | |
|---|---|---|---|
| 5,254,466 | 10/1993 | Picataggio et al. | 435/142 |
| 5,620,878 | 4/1997 | Picataggio et al. | 435/142 |

FOREIGN PATENT DOCUMENTS

| | | |
|---|---|---|
| 2140133 | 2/1973 | Germany . |

OTHER PUBLICATIONS

"Microbial Production of Long–Chain Dicarboxylic Acids from n–Alkanes", Agricultural and Biologiccal Chemistry, vol. 35, No. 13, Jan. 1, 1971 pp. 2033–2042.

"Antifungal Properties of Alpha, Omega–Alkanedicarboxylic acids and Their Dimethyl Esters", Can J. Microbiol., vol. 22, 1976, pp. 1198–1201.

*Primary Examiner*—Jean C. Witz
*Attorney, Agent, or Firm*—Noreen C. Johnson; Douglas E. Stoner

[57] ABSTRACT

This invention provides a low-cost method of producing α,ω-alkanedicarboxylic acids. Particular bioconversion conditions result in highly efficient conversion of fatty acid, fatty acid ester, or alkane substrates to diacids. *Candida tropicalis* AR40 or similar yeast strains are grown in a medium containing a carbon source and a nitrogen source at a temperature of 31° C. to 38° C., while additional carbon source is continuously added, until maximum cell growth is attained. Within 0–3 hours of this point, substrate is added to the culture to initiate conversion. An α,ω-alkanedicarboxylic acid made according to this method is also provided.

17 Claims, 1 Drawing Sheet

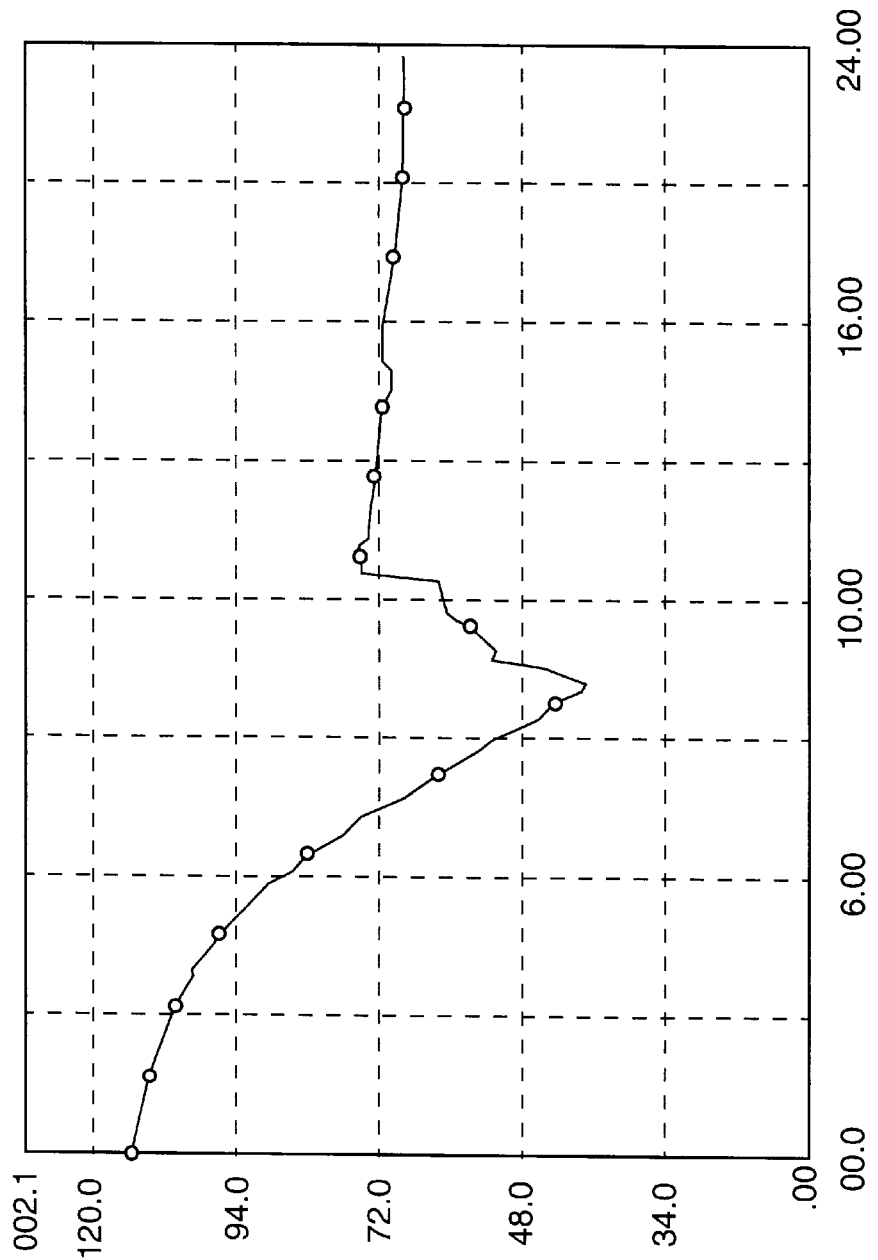

METHOD FOR HIGH SPECIFIC BIOPRODUCTIVITY OF α,ω-ALKANEDICARBOXYLIC ACIDS

This invention was made with Government support under Government Contract No. DE-FC36-95G010099, awarded by the Department of Energy. The Government has certain rights in this invention.

BACKGROUND OF THE INVENTION

1. Field of the Invention

This invention relates to the field of commercial biocatalytic production of chemical intermediates useful in the manufacture of high quality engineering thermoplastics. It provides a fermentation process for the production of α,ω-alkanedicarboxylic acids by yeast using readily available raw materials which achieves a high specific productivity. More specifically, the invention provides fermentation conditions which yield optimal performance of the yeast biocatalyst in the conversion of fatty acids, fatty acid esters, or alkanes to α,ω-alkanedicarboxylic acids.

2. Description of the Prior Art

Long-chain α,ω-alkanedicarboxylic acids with a carbon number of nine or greater (hereinafter referred to as diacids) are used as intermediates in the synthesis of a wide variety of chemical products, particularly in the production of plastics and other bulk specialty chemicals. In particular, these diacids are used in the production of a copolyestercarbonate (LEXAN™) which retains high impact strength, the hallmark of polycarbonate resin, while offering superior melt and flow characteristics relative to standard (bisphenol-A; BPA) polycarbonate. These properties make plastics which are useful for applications requiring light, thin-walled yet strong parts.

Diacids are currently produced almost exclusively by non-biological conversion processes, based upon the use of nonrenewable petrochemical feedstock. These multi-step chemical conversion processes typically produce unwanted hazardous byproducts which both result in yield losses and must be destroyed before they are released to the environment. Disposal of a hazardous waste stream greatly adds to the cost of production. In addition, the organic chemical synthesis of long-chain diacids is limited by the starting materials used, and each chemical synthesis process can produce only one species of diacid.

For example, according to prior art methods, dodecanedioic acid is produced by a multi-step chemical conversion process that has significant limitations and disadvantages. Because the synthetic process begins with the starting material butadiene (a 4-carbon petrochemical), the only diacids which can be synthesized are those with a carbon number which is a multiple of four. In practice, only dodecanedioic acid is made by this process, and dodecanedioic acid is the longest straight chain diacid currently available using an industrial chemical synthesis process. The dodecanedioic acid process produces byproducts such as cyclooctadiene and vinyl cyclohexene, which result in yield losses, and nitrogen oxides, which are either released to the atmosphere or must be destroyed in a reduction furnace.

Production of diacids using bioconversion is a potentially promising method which may overcome some of the disadvantages of the current chemical processes. Among the advantages inherent in all biological conversion processes are the ability to use renewable resources as starting materials for the process rather than petrochemicals, and the ability to produce chemicals without also producing a hazardous waste stream, disposal of which is expensive. For example, diacids may be produced from inexpensive long-chain fatty acids, which are readily available from renewable agricultural and forest products such as soybean oil, tallow, corn oil, and tall oil, without the production of the dangerous waste products discussed above.

Diacids are produced in only a single step when a biological process is used. Moreover, a bioconversion process can be adapted easily to produce a wide range of diacids, since the biocatalyst accepts a variety of starting materials. Therefore, a bioconversion method can produce diacids of different lengths which were unavailable for practical reasons using prior art chemical methods.

Of particular importance, a biocatalyst can produce diacids with longer chain lengths. Diacids with a carbon number of 16 or 18 could be produced using the same basic bioconversion which produces other diacids. These longer chain diacids are effective at lowering of melt viscosity in the copolyestercarbonate at a lower diacid concentration than the C12 diacid, and are thus more economical to use. Using prior art methods, however, these longer chain diacids can not be produced commercially and are currently unavailable for widespread use.

More importantly from a business perspective, however, biological conversion processes have the potential to produce diacids for a lower cost than the currently available chemical process. To do this, any biotechnological process must be able to utilize inexpensive, easily available organic substrates as starting materials, and convert those substrates to the desired diacid product with high efficiency.

The biological conversion process for production of long chain aliphatic diacids is carried out by batch fermentation. The batch fermentation process consists of two phases: growth and conversion (or transformation). The growth phase is initiated by inoculating a batch fermenter containing a nutrient medium with the yeast biocatalyst. During this phase of the process, the cells increase in number to a cell density which is dependent on many factors, including the cell type and the nutrient content of the medium. Growth continues in the batch fermenter under selected conditions for a selected period of time or until a selected cell density is reached, at which time the fatty acid, fatty acid ester, or alkane substrate is added to initiate the conversion phase, during which the desired product is formed. During conversion, an excess of substrate is always maintained. A carbon source (cosubstrate) such as glucose also is added throughout the conversion phase to provide an energy source for the yeast. When conversion is completed, the yeast biomass is separated from the fermentation medium, and the diacid product is recovered and purified from the solution.

Yeast produce diacids from fatty acids through the ω-oxidation pathway. The first and rate-limiting step is the oxidation of the terminal methyl carbon to produce an ω-hydroxy acid. This step is mediated by a membrane-bound enzyme complex consisting of a cytochrome P450 monooxygenase and an associated NADPH cytochrome reductase. Two additional enzymes, an alcohol oxidase and an aldehyde dehydrogenase, further oxidize the alcohol to create an ω-aldehyde acid and then the corresponding α,ω-dicarboxylic acid. Several yeasts are known to produce various diacids when grown on fatty acid, fatty acid ester, or alkane substrates, for example *Candida tropicalis, C. albicans, C. cloacae, C. guillermondii, C. intermedia, C. lipolytica, C. maltosa, C. parapsilosis,* and *C. zeylenoides*.

These yeasts have a number of limitations which prevent their efficient use for the commercial production of diacids, however. In general, the biocatalytic fermentations known heretofore have produced too low a total yield of diacid relative to the fatty acid or alkane starting material to be practically useful. In addition, the yeast biocatalysts produced too large a quantity of unwanted byproducts such as 3-hydroxy acids, and shorter chain acids and diacids due to β-oxidation which reduce the yield and necessitate further steps in the process to remove the impurities. In summary, the prior art biofermentation processes do not produce an efficient conversion of the starting material into the desired diacid product.

The rate of conversion of the starting material to the desired end product (the specific productivity, grams of product formed per liter fermentation medium per hour) also is a key factor in the total effective cost of commercial biological production of diacids. Therefore increasing the specific productivity of the bioconversion process can significantly reduce the diacid production cost.

Recently, genetically modified strains of the yeast *Candida tropicalis* have been developed in the hope of increasing the specific production of diacids above that obtainable with wild type yeast. U.S. Pat. No. 5,254,466 discloses a genetically modified strain of *C. tropicalis* (strain H5343, ATCC No. 20962) in which the genes coding for enzymes in the first step of fatty acid β-oxidation have been disrupted so that the yeast can no longer use fatty acids as a carbon source. In this strain, β-oxidative degradation of the substrate and product leading to a progressive shortening of the alkane chains does not occur. This yeast is able to produce highly pure diacids in substantially quantitative yield, without the production of these unwanted byproducts.

U.S. Pat. No. 5,620,878 discloses a *C. tropicalis* strain termed AR40 (ATCC No. 20987) which has been further modified. Multiple copies of cytochrome P450 and reductase genes of the 4-hydroxylase system have been introduced. This genetic manipulation resulted in a yeast with increased ω-hydroxylase activity and even greater specific productivity (g/L/hr) of diacids from long-chain fatty acids. Nevertheless, the preferred process described for genetically modified yeasts in U.S. Pat. No. 5,254,466 (*C. tropicalis*, strain H5343, ATCC No. 20962); in U.S. Pat. No. 5,620,878; and in a related journal publication, (S. Picataggio, Bio/Technology 10:894–8 (1992)), do not produce the diacids with sufficient specific productivity for their commercial production to be economically feasible.

For biological production of diacids as bulk chemical intermediates to be commercially practical, the cost of production must be significantly reduced. There is consequently a need for a biological fermentation process in which specific productivity is enriched and the efficiency of diacid production is maximized.

SUMMARY OF THE INVENTION

Accordingly, the inventors have developed a process for producing α,ω-alkanedicarboxylic acids, comprising culturing *Candida tropicalis* cells during a growth phase in a culture medium containing at least a nitrogen source and a carbon source at a temperature of about 31° C. to about 37° C. wherein additional carbon source is continuously added throughout the growth phase; initiating a conversion phase by addition of a substrate selected from the group consisting of fatty acids, fatty acid esters, and alkanes within about 0–3 hours after the maximum growth rate of the culture cells is attained; and continuing culturing the cells during the conversion phase with addition of additional carbon source. Another aspect of the invention is a process for producing α,ω-alkanedicoarboylic acids comprising culturing *Candida Tropicalis* AR40 cells during a growth phase in a culture medium containing at least a nitrogen source and glucose at a temperature of about 33° C. to about 35° C. wherein additional glucose is continuously added thoughout the growth phase at a rate of about 2.2 g/L/h; initiating a conversion phase by addition of a substrate selected from the group consisting of methyl myristate and oleic acid within about 0.5 to about 2 hours after the maximum growth of cells is attained; and continuing culturing the cells during the conversion phase at a pH of about 7 to about 8 and a temperature of about 27° C. to about 33° C. Yet another aspect of the invention is an α,ω-alkane-dicarboxylic acid made according to the above-described processes.

BRIEF DESCRIPTION OF THE DRAWINGS

FIG. 1 is a graphical representation of the dissolved oxygen concentration of a yeast culture during a typical fermentation.

DISCLOSURE OF THE INVENTION

The inventors have developed an economical method for the manufacture of α,ω-alkanedicarboxylic acids using a biological conversion process which attains a greatly increased specific productivity for α,ω-alkanedicarboxylic acids. This is accomplished through the selection and use of a preferred set of fermentation conditions for the growth of the yeast that catalyzes the biological conversion which results in the optimal conversion of a fatty acid, fatty acid ester, or alkane substrate to its corresponding diacid. In particular, we have discovered that a certain growth period with a temperature preferably in the range of 31–37° C., and continuous addition of a carbon source results in the proliferation of yeast with high specific diacid productivity. The highest specific activity is achieved by starting the conversion phase at or soon after the attainment of the maximum growth rate. Preferred conditions during the conversion phase which elevate the specific productivity of diacids are a temperature range of about 27° C. to about 33° C. and an initial pH range of about 7 to about 8.

Using conditions representative of the prior art (see Example 5), we have previously demonstrated peak diacid specific productivity of 1.0 g/L/h and an average productivity of 0.6 g/L/h, yielding a final diacid concentration of 75 to 80 g/l, using methyl myristate as the test substrate. Biofermentative production using the same fermenter, yeast culture, and other materials according to the invention results in productivities significantly higher than those attainable in the prior art, with peak diacid specific productivity of 1.8 g/L/h and average specific productivity of 1.0 g/L/h, yielding a final diacid concentration of 75 to 80 g/L.

During the growth phase, the most important factors affecting specific productivity of diacids were the temperature, continuous availability of glucose to the culture, the rate of addition of glucose to the culture, and the particularly the timing of the initiation of the conversion phase. In contrast, pH during the growth phase appeared to be relatively unimportant, since reasonably high productivity values were obtained throughout the entire pH range tested (pH 4.0 to pH 6.4).

One of the most important factors in maximizing the specific rate of conversion from substrate to the desired diacid product was beginning the conversion phase at the point when the yeast were growing at their maximum rate, or soon thereafter. At this point, the yeast's metabolism seems to be operating at near its fastest rate and is therefore appears to develop the greatest activity for converting the substrate to diacid product.

To determine the optimal time to begin the conversion phase, the growth of the yeast culture can be conveniently monitored by measuring the dissolved oxygen content in the fermentation medium. During growth, the aeration rate of the batch fermenter is kept constant, and the DO gradually decreases as the culture grows and demands more oxygen, eventually reaching a minimum which defines the point of maximum oxygen demand. The dissolved oxygen reflects the metabolism (growth) of the cells, because the dissolved oxygen concentration is lowest when the biological oxygen demand of the culture is highest. In practice, with continuous monitoring of the DO concentration, when the DO reaches a minimum and begins to rise (and the oxygen demand of the growing cells reaches a peak and begins to diminish), the maximum growth rate has been reached. FIG. 1 demonstrates this phenomenon in a typical fermentation. Dissolved oxygen can be measured by any suitable method, for example, by a polargraphic dissolved oxygen electrode. Other methods of monitoring the growth of the yeast culture are readily apparent to those of ordinary skill in the art, such as cell counts, turbidityor cell dry weight, etc., but these methods measure cell density rather than rate of cell growth, and usually involve a substantial delay between sampling and obtaining the measured result.

A likely reason why beginning the conversion phase soon after the point of maximum growth rate is important to the specific conversion rate is that it initiates induction of the ω-oxidation pathway under conditions of yeast culture high metabolic activity. Shortly after the DO minimum point in a typical prior art fermentation, the glucose in the culture medium is depleted. Presumably, after maximum growth is achieved, if the culture becomes depleted of a carbon source or other nutrients due to high cell density, the culture could be expected to go into a stationary or resting mode, in which metabolism is decreased. If the culture is allowed to enter a resting phase just as conversion begins, the induction of ω-oxidation activity in the culture also could be reduced.

Conversion should be initiated by addition of substrate within about 0 hours to about 3 hours after maximum growth is reached, preferably from about 0.5 hours to about 2.0 hours. In a fermentation where the time to reach a DO minimum is, for example, 8 hours, conversion should be initiated at about 8 hours to about 11 hours after the growth phase was begun or preferably at about 8.5 to about 10 hours after the growth phase was begun. If the duration of growth is different, the time of initiation of the conversion phase should be adjusted to account for this. As a practical matter, it is not always possible to start the conversion phase at exactly the moment of maximum growth, and exact timing is not necessary to practice the invention or to achieve high specific productivities. However, allowing too much time to pass between the attainment of full growth and start of the conversion phase is at best an unneeded waiting period and at worst may result in lower activity from the biocatalyst culture.

In addition to carefully monitoring the growth of the yeast culture, it is also important to take steps to ensure that a carbon source is consistently available to the yeast at all times, and that at no time does the culture become starved for carbon source. The inventors have found that if the glucose was added only at the beginning of growth, the culture became starved for glucose at the end of the growth period. Continued addition of glucose during the growth phase, and in particular, immediately prior to addition of substrate, however, has been found to be helpful in boosting the productivity of the culture.

Therefore, an important element of the present invention which is beneficial for obtaining high productivity is the practice of withholding a portion of the total amount of carbon nutrient from the initial culture medium and adding a carbon source continuously over the growth period. This technique is known as fed-batch growth.

We have observed that shortly after the point of maximum growth rate, whether glucose has been continuously added or not, the glucose in the growth medium is depleted (i.e., there is no measurable glucose remaining). With simple batch growth, there is no more glucose available to the yeast from this point until continuous glucose addition is started in the conversion phase. With fed-batch growth, glucose is still being added continuously throughout the rest of the growth phase and throughout the conversion phase. Therefore, even though there is no measurable glucose concentration in the fermenter after the period of maximum growth (because it is rapidly consumed by the very active yeast culture), the yeast is always supplied with some glucose and is not permitted to starve with respect to the carbon source.

TABLE 1

Advantage of Fed-Batch Growth in Increasing Diacid Productivity.

| Experiment | Temp (° C.) | Length of Growth Phase (h) | Batch (B) or Fed-Batch (FB) Mode[1] | Productivity of Diacid (g/L/H) |
|---|---|---|---|---|
| A | 33 | 12 | B | 1.02 |
| B | 33 | 12 | FB | 1.17 |

[1]Fed-Batch glucose feed rate = 1.1 g/L/h.

Experimental data show the advantage of fed-batch growth as shown in Table 1. Cells grown under fed-batch growth conditions, with other conditions being similar, yielded higher amounts of diacid product per liter per hour than cells grown under regular batch growth conditions.

The rate of glucose addition during the growth phase is also an important variable in the production of diacids. In experiments with methyl myristate as the substrate, increasing the rate of glucose addition resulted in significantly higher production of diacid relative to the intermediate hydroxyacid product. Thus, keeping the availability of glucose consistently higher tended to increase the yeast's ability to completely convert more substrate to the final diacid product.

The initial fermenter charge can contain about 10 g/L to about 30 g/L glucose, or preferably about 20 g/L glucose (preferably from an inexpensive source such as unrefined corn syrup). During the growth phase, glucose can be added to the fermenter at a rate in the range of about 1 g/L/h to about 4 g/L/h, preferably about 1.5 g/L/h to about 3 g/L/h or most preferably about 2.2 g/L/h. The addition of more total glucose is not necessary to maintain the metabolic activity of the culture using this method as long as some glucose is always available for the culture. Note that the total glucose added to the system by the end of the growth phase in a fed-batch culture may be more or less than the total glucose used in a typical medium for simple batch growth. Other carbon sources may be used, for example fructose, maltose, glycerol, etc.

To maximize the hourly production of diacids for each fermentation batch, methods whereby the duration of the growth phase could be shortened were investigated. A shorter growth phase is beneficial for productivity because it shortens the overall batch fermentation cycle, increasing the number of fermentations which can be performed over time. Higher growth temperature is also desirable because cooling of the fermenter with typical process cooling water is more efficient when operating at a higher temperature. We have found that the growth phase can be safely shortened by operating the fermentation at higher temperatures during the growth phase.

Commonly, batch fermentations of diacid producing yeast are performed at about 30° C. with a growth period of about 18 hours. at a temperature of 30° C. By increasing the temperature to the range of about 33° C. to about 35° C., the yeast were able to reach full growth in as little as only 8 hours. Yet, forcing the yeast to grow at a faster rate did not adversely affect productivity during the conversion phase if the temperature was kept at 37° C. or lower during growth. In general, temperatures of 31° C. to about 37° C. may be used with this invention, preferably about 33° C. to about 35° C. Using temperatures during the growth phase between about 33° C. and about 35° C. resulted in relative short growth phase periods of about 7.5 to about 8.5 hours.

It is important to remember that as the temperature is changed, the time of growth necessary to reach the maximum growth rate also changes, therefore, the length of the growth phase must be monitored for each fermentation condition so that conversion may be initiated at the appropriate time. If this is not done, the highest specific productivity at any given temperature will not be attained. In our hands with a typical growth medium and a 10& inoculum, in the preferred temperature range of 33° C. to 35° C., the point of maximum growth rate occurs at about 7.5 to 8.5 hours after inoculation, and thus the preferred length of the growth phase would be in the range of about 8 to 10.5 hours.

It should be noted that certain combinations of lower growth temperatures and longer growth phases can also yield relatively high specific productivity. For example, we have obtained relatively high specific productivity at a growth temperature of 26° C. and an 18 hour growth phase, as long as conversion is initiated at the appropriate time, at or soon after the culture reaches maximum growth. As discussed above, however, for economic reasons combinations of higher temperatures and shorter growth phases are more preferable.

The conversion phase is begun with the initiation of continuous addition of substrate to the fermenter. Continuous addition of the carbon source also is maintained. Temperature, pH, and the rate of glucose addition may all be adjusted at this time for optimal conversion of the substrate. Certain particular conversion phase conditions were found to produce unexpectedly high yields of diacid. Productivity is enhanced by using a higher initial rate of glucose addition than previously used during this phase (see Examples 2 and 3), and in contrast to the growth phase, pH was found to have a significant effect on fermentation performance.

The substrate is added at a rate sufficient to provide an excess of substrate with respect to the rate of conversion of substrate to diacid product. However, with fatty acid substrates such as oleic acid, it is detrimental to the conversion rate to allow accumulation of the substrate to concentrations abouve about 5–10 g/L. This is in contrast to the prior art, which cites substrate concentrations of 10-2- g/: as a preferred condition (cf. U.S. Pat. No. 5,620,878).

During conversion, glucose should be added at an initial rate of about 1 g/L/h to about 4 g/L/h, desirably about 1.2 g/L/h to about 3.8 g/L/h and preferably about 2.1 g/L/h to about 3.8 g/L/h. Because we have found that over the range of 1.2 g/L/h to 3.8 g/L/h, a higher fulucose addition rate over the first 24 hours of conversion phase results in higher specific productivity, the most preferred glucose addition rates are about 2.4 g/L/h for the first 5–24 hours of conversion and about 1.8 g/L/h thereafter. Note that maintaining tooo high a rate of glucose addition throughout the conversion can leas to glucose accumulation, which is undesirable.

The process temperature is also readjusted, if necessary due to increased temperature during growth, at the beginning of the conversion phase. Suitable temperatures during conversion range from about 27° C. to about 33° C., preferably about 30° C.

The pH which is optimal for conversion of a substrate to a diacid depends on the substrate used and the other fermentation conditions. For fatty acid esters, such as fatty acid methyl esters, after the period of growth, the conversion phase may be started at a pH of about 7 to about 8.3, preferably about 7.0 to about 7.5 for maximum productivity. Within the range of pH 7 to 8.3, a lower pH over the first 24 hours of conversion phase results in a higher specific productivity. After the first 24 hours of conversion, the pH is preferably adjusted upward to about pH 8,8 to maintain diacid product solubility. When fatty acids are used as substrates, the conversion phase pHis about 7.0 to about 8.8, preferably about 7.8.

Note that all rates of glucose (corn syrup) addition are calculated on a dry glucose basis and on the basis of the initial fermenter volume. In addition, the specific productivity data discussed in the specification and in the examples aree based on the final liquid volume of the fermenter. Some of the prior literature cites specific productivity numbers higher than those reported in the examples. However, the prior literature used the initail liquid volume of the fermenter as the basis for the specific productivity calculation. Since liquid volume of the fermenter increases significantly throughout the process, the initial volume basis results in substantially higher calculated specific productivity than the final volume basis used here. Example 5 is representative of the specific productivity that can be achieved with the prior art using our calculation methods.

TABLE 2

Representative Bioconversion Media for Production of Diacids.
A. Fermentation Medium

| Component | Concentration |
|---|---|
| corn steep liquor[1] | 9.0 g/L |
| ammonium sulfate | 8.0 g/L |
| $KH_2PO_4$ | 2.0 g/L |
| $K_2HPO_4$ | 1.0 g/L |
| $MgSO_4.7H_2O$ | 0.5 g/L |
| NaCl | 0.1 g/L |
| $CaCl_2.2H_2O$ | 0.1 g/L |
| $H_3BO_3$ | 500 µg/L |
| $MnSO_4.H_2O$ | 400 µg/L |
| $ZnSO_4.7H_2O$ | 400 µg/L |
| $FeCl_3.6H_2O$ | 200 µg/L |
| $NaMoO_4.2H_2O$ | 200 µg/L |
| KI | 100 µg/L |
| $CuSO_4.5H_2O$ | 40 µg/L |
| Antifoam[2] | 4 g/L |

[1]Cargill Heavy Corn Steepwater, a nitrogen source
[2]Hoday M-10

The principles and practice of this invention are illustrated by the following examples.

EXAMPLES

1. Production of 1,14-Tetradecanedioic Acid from Methyl Myristate by Bioconversion.

A stirred, aerated fermenter with a working volume of 5 L was charged with 2.27 L medium as described in Table 2, also containing 20 g/L (glucose basis) Cargill CLEAR-SWEET™ unrefined 95% dextrose corn syrup. The medium was inoculated with a 10% inoculum of *C. tropicalis* AR40 to yield a liquid volume of 2.5 L. The culture was grown at 35° C. and pH 6.0, sparging with air at a rate of 3.0 L/min for 9 hours, during which time glucose was continuously added at 3.9 g/L/h. The DO minimum (maximum growth rate) occurred at 8.25 hours. Conversion was initiated by addition of methyl myristate (Emery 2214 methyl myristate, 95%; Henkel, Cincinnati, OH) at a rate of 2.1 g/L/h (6.6 ml/h) at 9 hours. The pH was simultaneously raised to 8.2, and the temperature lowered to 30° C. Glucose addition to the fermenter was adjusted to 2.0 g/L/h. After 24 hours of conversion, the diacid concentration was 34.5 g/L, for an average specific productivity over the conversion phase of 1.44 g/L/h.

2. Production of 1,14- Tetradecanedioic Acid from Methyl Myristate by Bioconversion under Relatively High Glucose Addition Rate during Conversion.

The fermenter was charged with the Medium in Table 2 containing 20g/L glucose and inoculated as in Example 1. The culture was grown under the conditions described in Example 1, except glucose addition was at the rate of 2.1 g/L/h. The DO minimum occurred at 7.75 hours and conversion was initiated after 9.6 hours by addition of methyl myristate as in Example 1. During conversion, the temperature was 30C, the pH was 8.3, and the rate of glucose addition was 2.9 g/L/h. After 20.5 hours of conversion, the diacid concentration was 32.2 g/L for an average specific productivity over the conversion phase of 1.57 g/L/h.

3. Production of 1,14-Tetradecanedioic Acid from Methyl Myristateby Bioconversion under Relatively Low Glucose Addition Rate during Conversion.

Fermentation was performed as in Example 2, except that glucose was added during the growth at 2.0 g/L/h. The DO minimum occurred at 8/1 hours and conversion was begun after 10.3 hours of growth. The conversion phase was conducted as in Example 3, except that the glucose addition rate was 2.0 g/L/h. After 24 hours of conversion, the diacid concentration was 27.6 g/L for an average specific productivity over the conversion phase of 1.15 g/L/h. The differences during the growth phase in the processes of Examples 2 and 3 are not considered to be important to their relative performance. The improvement in productivity of Example 2 relative to Example 3 is attributed to the difference in conversion phase glucose addition rates.

4. Production of 1,14- Tetradecanedioic Acid from Methyl Myristate by Bioconversion under Relatively High Glucose Addition Rate during Conversion and Low Initial Conversion pH Conditions.

The fermenter was charged and inoculated as in Example 1. The culture was grown as in Example 1, with a glucose addition rate during growth of 2.3 g/L/h. The DO minimum occurred at 7.55 hours. Conversion was initiated after 9 hours at a pH of 7.3 and glucose addition rate of 2.5 g/L/h. Again, methyl myristate was the substrate, as in Example 1. After 22.5 hours of conversion, the diacid concentration was 32.7 g/L for an average specific productivity over the conversion phase of 1.45 g/L/hr.

5. Production of 1,14- Tetradecanedioic Acid from Methyl Myristate by Bioconversion under Conditions Mimicking Prior Art Methods.

This example is not part of the invention, but is presented for comparison of the specific productivity obtained with the invention with that obtained under growth conditions representative of the prior art. The fermenter was charged with Medium 1 additionally containing 40 g/L glucose and inoculated as in Example 1. The culture was grown at 30° C., pH 6.5, at an aeration rate of 3.0 L/min for 18 hours with no glucose addition during the growth phase. The DO minimum occurred at 11 hours. Conversion was initiated at 18 hours by beginning addition of methyl myristate at 2.0 g/L/h (6.2 ml/h). The pH was adjusted to 8.2 and corn syrup was continuously added at 1.9. g/L/h. After 23.5 hours of conversion, the diacid concentration was 19.8 g/L for an average specific productivity over the conversion phase of 0.82 g/L/h.

6. Production of 1,14- Tetradecanedioic Acid from Methyl Myristate by Bioconversion under Conversion Conditions Mimicking Prior Art Methods.

This example is not part of the invention, but is presented for comparison of the specific productivity obtained with the invention with that obtained under growth conditions representative of the prior art. Fermentation conditions were as in Example 4, except that glucose was added at 1.9 g/L/h during the growth phase, conversion was initiated at 9 hours, and during conversion the pH was 8.2 and the glucose addition rate was 2.0. g/L/h. After 24 hours of conversion, the diacid concentration was 26.4 g/L for an average specific productivity over the conversion phase of 1.10 g/L/h. The conversion (but no the growth) condition s of this Example were similar to prior art mehtods. The improvement is productivity of Example 4 relative to Example 6 is attributed to the combination of the higher glucose addition rate during conversion and the lower conversion pH of Example 4.

7. Production Dicarboxylic Acid from Oleic Acid by Bioconversion.

The Fermenter was charged and inoculated as in Example 1. Growth conditions were 35° C., pH 6.0, and glucose addition at 2.3 g/L/h. After 9 hours of growth phase, the conversion phase was started by continuous addition of commercial oleic acid (Emersol 213, a mixture of fatty acids with a cis-C 18:1 fatty acid content of about 70%) at 1.4 g/L/h (4 ml/h). During conversion, the temperature was 30° C., the glucose feed rate was adjusted to 2.5 g/L/h, and the pH was 7.8. Hoday M-10 antifoam (Calgene Chem., Skokie Illinois) was added automatically to control foaming. After 7 hours of conversion,the glucose addition rate was reduced to 1.8 g/L/h and was further reduced at subsequent times as necessary to provent accumulation of glucose. After 97 hours of conversion, the total diacid concentration was 94 g/L for an average specific productivity over the conversion phase of 0.97 g/L/h.

8. Cutituring Techniques and Methods.

Stock culture was prepared by inoculating 25 ml Difco YM Broth in a 250 ml conical flask with 2.0 ml (about 108 viable cells per ml) of seed culture of *C. tropicalis* AR40, ATCC No. 20987 and incubating at 30° C. and 250 rpm (New Brunswick Model G-25 shake incubator) for 24 hours. The master feed stock culture was preserved in 1.5 ml aliquots by mixing 0.75 ml of the above culture with an equal volume of sterile glycerol solution (50% in water) and storing immediately in a freezer at −80° C.

Preculture was prepared by inoculating 20 ml Difco YM Broth in a 250 ml conical flask with 1.5 ml of thawed master feed stock culture (containing approximately 108 cells per ml.) and incubating at 30° C. and 250 rpm for 24 hours. Main fermenter inoculum culture was prepared by inoculating 500 ml medium containing 60 g/L glucose, 6.7 g/L Difco Yeast Nitrogen Base, 3 g/L ammonium sulfate, 3 g/L Difco Yeast Extract, 1 g/L potassium phosphate dibasic, and 1 g/L potassium phosphate monobasic in a 2 liter baffled conical flask with 5 ml of preculture (1% inoculum) and incubating at 30° C. and 250 rpm for 24 hours.

Bioconversions were carried out in both B. Braun Biostat E and New Brunswick Scientific BioFlo III fermenters, each with 5 liters nominal working liquid capacity, equipped with mechanical stirring, temperature and pH control, automatic antifoam addition, filter-sterilized air sparging, and dissolved oxygen probe. No difference was found between the Biostat E and BioFlo III for these bioconversions.

Prior to inoculation, the culture vessel containing the ammonium sulfate, potassium phosphates and corn steep liquor was sterilized for 30–40 min at 121° C. The glucose solution (corn syrup diluted to 50% (w/v) glucose) was sterilized separately and added to the sterilized medium after cooling, along with the antifoam (separately sterilized) and the remaining medium ingredients (filter-sterilized). The culture was grown using 6N NaOH (Examples 1–6) or 6N KOH (Example 7) and 4N $H_2SO_4$ for pH control, stirring at 900 rpm. At the end of the growth phase cell count measurements typically showed about $10^9$ viable cells per ml.

What is claimed is:

1. A process for producing α,ω-alkanedicarboxylic acids, comprising:
   (a) culturing Candida tropicaliscells during a growth phase in a culture medium containing at least a nitrogen source and a carbon source, which is glucose present at a concentration of about 10 g/L to about 30 g/L, at a temperature of about 33° C. to about 35° C. wherein additional glucose is continuously added through the growth phase at a rate of about 1 g/L/h to about 4 g/L/h;
   (b) initiating a conversion phase by addition of a substrate selected from the group consisting of fatty acids, fatty acid esters and alkanes within 0–3 hours after the maximum growth of the cultured cells is attained, and
   (c) continuing culturing the cells during the conversion phase wherein glucose is added during the conversion phase at a rate of about 1 g/L to about 4 g/L.

2. A process according to claim 1, wherein the glucose is provided as unrefined corn syrup.

3. A process according to claim 1, wherein the glucose in the culture medium is present at a concentration of about 20 g/L.

4. A process according to claim 1, wherein the glucose is continuously added through the growth phase at a rate of about 1.5 g/L/h to about 3 g/L/h.

5. A process according to claim 4, wherein the glucose is continuously added through the growth phase at a rate of about 2.2 g/L/h.

6. A process according to claim 1, wherein the glucose is added during the conversion phase at a rate of about 1.2 g/L to about 3.8 g/L.

7. A process according to claim 6, wherein the glucose is added during the conversion phase at a rate of about 2.1 g/L to about 3.8 g/L.

8. A process according to claim 1, wherein the glucose is added during the conversion phase at a rate of about 2.4 g/L/h for the first 5–25 hours and about 1.8 g/L/h thereafter.

9. A process according to claim 1, wherein the substrate is a fatty acid.

10. A process according to claim 9, wherein the fatty acid is oleic acid.

11. A process according to claim 1, wherein the substrate is a fatty acid ester.

12. A process according to claim 11, wherein the fatty acid ester is methyl myristate.

13. A process according to claim 1, wherein the substrate is an alkane.

14. A process according to claim 1, wherein the maximum growth rate of the cultured cells is determined by monitoring the dissolved oxygen of the culture.

15. A process according to claim 1, wherein the conversion phase is initiated by adding substrate within 0.5 to about 2 hours after the maximum growth rate of the cultured cells is attained.

16. A process according to claim 1, wherein the Candida tropicalis cells are C. tropicalis, strain AR40.

17. A process for producing α,ω-alkane dicarboxylic acids comprising culturing Candida tropicalis AR40 cells during a growth phase in a culture medium containing at least a nitrogen source and glucose at a temperature of about 33° C. to about 35° C. wherein additional glucose is continuously added through the growth phase at a rate of about 2.2 g/L/h; initiating a conversion phase by addition of a substrate selected from the group consisting of methyl myristate and oleic acid within about 0.5 to about 2 hours after the maximum growth of cells is attained; and continuing culturing the cells during the conversion phase at a pH of about 7 to about 8 and a temperature of about 27° C to about 33° C.

* * * * *